United States Patent [19]

Rigby et al.

[11] Patent Number: 5,254,117
[45] Date of Patent: Oct. 19, 1993

[54] MULTI-FUNCTIONAL ENDOSCOPIC PROBE APPARATUS

[75] Inventors: Larry Rigby; Eric Steckel, both of Salt Lake City; Dixon Ford, Farmington, all of Utah

[73] Assignee: Alton Dean Medical, Woods Cross, Utah

[21] Appl. No.: 854,108

[22] Filed: Mar. 17, 1992

[51] Int. Cl.$^5$ ............................................. A61B 17/36
[52] U.S. Cl. ......................................... 606/46; 606/42; 606/49
[58] Field of Search ...................... 606/32, 33, 34, 39, 606/40, 41, 42, 45, 46, 47, 48, 49, 50, 37, 43; 604/4, 783, 784, 790, 20, 21, 22

[56] References Cited

U.S. PATENT DOCUMENTS

| | | | |
|---|---|---|---|
| 4,408,598 | 10/1983 | Ueda | 128/4 A |
| 4,617,915 | 10/1986 | Arakawa | 128/4 |
| 4,753,234 | 6/1988 | Martinez | 604/22 |
| 4,924,851 | 5/1990 | Ognier et al. | 128/4 |

FOREIGN PATENT DOCUMENTS 8605379 9/1986 World Int. Prop. O. ............ 606/45

*Primary Examiner*—Stephen C. Pellegrino
*Assistant Examiner*—Michael Peffley
*Attorney, Agent, or Firm*—Workman, Nydegger & Jensen

[57] ABSTRACT

A multi-functional endoscopic probe apparatus to selectively apply either a low or high frequency voltage to cut and cauterize. The apparatus has an elongated multi-lumen tube that is attached to a pistol grip having a multiplicity of functions contained thereon. The multi-lumen tube has a first lumen for the passage of either a high or a low pressure irrigation stream therethrough, a second lumen for suction to remove excess fluid and debris, and a third lumen for the passage of a slidably extendable and retractable electro-surgical cutting tip. The pistol grip handle has a wheel which enables the surgeon to rotate the multi-lumen tube containing the surgical cutting tip relative to the pistol grip. A plurality of push-button valves enable the selective application a negative pressure for withdrawing excess fluids and removing incident tissue debris from the surgical site and to operatively apply a flood irrigation stream or a precise irrigation stream to the surgical site to wash and cleanse the tissue. A multi-position electric switch directs either a low or a high frequency voltage to an electro-surgical cutting tip in order to cut and/or cauterized the tissue in contact therewith.

39 Claims, 9 Drawing Sheets

MULTI-FUNCTIONAL ENDOSCOPIC PROBE APPARATUS

BACKGROUND

1. The Field of the Invention

Broadly conceived, the present invention relates to surgical probe devices or wands employed in the field of endoscopic surgery. More particularly, the present invention relates to an endoscopic probe that performs multiple functions, including electro-surgical cut and cautery, two modes of irrigation, suction, and rotational positioning of the electro-surgical tip.

2. The Background of the Invention

In medical practice, electro-coagulation involves the application of a highly concentrated heat source, usually from a heated metallic instrument, to cut and cauterize tissue during a surgical procedure. As opposed to the cold steel of a standard surgical knife, the heated blade of an electro-coagulation instrument quickly and efficiently cuts through tissue while simultaneously cauterizing the exposed layers. The cauterization process seals the exposed tissue surfaces and prevents loss of blood through bleeding.

To achieve the cut and cauterization of the intimal tissue at the surgical site, there are two electrocautery devices commonly used in the art. The bipolar electrocautery device has a two pronged tip configuration with a high electric potential drawn between the two prongs of the bipolar cautery tip. When the surgeon directs the tip over tissue, the electric current passes through the tissue between the two prongs and is simultaneously cut and cauterized. The unipolar electrocautery device makes use of a single prong at the tip. An electric pad is placed underneath the patient's buttocks or thigh. When the surgeon places the unipolar cautery tip to contact the patient's tissue, the electric current is focused at the point where the tip meets the tissue such that the tissue gets simultaneously cut and cauterized.

Electro-cauterization techniques are typically performed after an incision is made through the patient's skin in order to expose the underlying operative area. For quite a number of surgical procedures, the incision made through the patient's skin is relatively large in order for the surgeon to expose a large enough section of the operative area such that the surgeon's hands and instruments can reach the surgical site. One problem with the requirement of a large incision through the patient's skin is increased trauma and longer recuperative periods for the patient. The result is increased hospital stays and related post-operative costs, and increased risk of complications.

In order to reduce the size of the incision made through the patient's skin, advances have been made in basic surgical procedures and related technologies. One procedure, known as endoscopy, has rapidly developed in the surgical arts as a preferred methodology for performing certain surgical procedures without having to make large incisions in the patient. Endoscopic procedures involve introducing one or more trocars through puncture wounds in the patient and then accessing the internal surgical site using instruments introduced through the trocars, and using an endoscope to view the operative site as the surgical procedure is performed.

An example of one such endoscopic procedure is laparoscopic cholecystectomy, which is now a preferred surgical modality for the treatment of gallstone disease. This procedure employs a high-resolution video endoscopy system with color monitors and a light source, a high-flow $CO_2$ insufflator, an endoscopic suction-irrigation system, and an electrocautery device to enable the surgeon to completely remove the gallbladder without the need for one or more relatively large incisions through the patient's abdominal wall. Further, the surgeon's hands do not enter the abdominal peritoneal cavity.

To initiate a laparoscopic cholecystectomy procedure, the surgeon inserts four trocar devices into the patient through four small puncture wounds. The inside diameter of the bore of each trocar device is typically either 5 mm or 10 mm, depending on the instrumentation that is to be placed down the bore. The surgeon will place down one trocar tiny instrumentation such as a $CO_2$ insufflator to distend the abdominal cavity with gas pressure. Another trocar will contain combined irrigation and suction equipment. A miniaturized camera and lighting equipment will be inserted down another trocar so that the operative area can be completely viewed from a color monitor placed nearby. Lastly, the surgeon will perform the cut and cautery portion of the surgical procedure through a fourth trocar using an electrocautery probe device.

The beneficial result of such endoscopic procedures is a decrease in overall morbidity rates otherwise inherent in such invasive surgical procedures. Since the patient has to recover from only four relatively small puncture wounds, the overall time of the hospital stay and the associated recuperative period is substantially minimized, resulting in decreased costs. In addition, the necessity for follow-up procedures is dramatically reduced, there is less risk of post-operative complications, and the patient can return to normal activity much more quickly.

Despite the benefits inherent in endoscopic procedures, disadvantages exist in the prior art as well. For example, when using a trocar the surgeon must repeatedly change instruments. This means removal of one device from within the trocar bore after a certain function is performed by that the same trocar in order to perform another specific function. One problem associated with the constant removal and insertion of various instrumentation is increased risk of infection of the internal organs and tissue of the patient. Another problem associated with the need to constantly insert and remove a series of different devices in order to perform the desired functions is that the overall procedure takes longer and is more complicated. Further, because the time duration for the entire procedure is lengthened, the patient is under the effects of anesthesia longer. The overall costs of the operation increase accordingly with the increase in complexity of the procedure and the increase in the time duration which the surgeon must devote to complete the surgical procedure.

BRIEF SUMMARY AND OBJECTS OF THE INVENTION

The apparatus of the present invention seeks to resolve a number of the problems which have been experienced in the art, as identified above. More specifically, the apparatus of this invention constitutes an important advance in the art as evidenced by the following objects and advantages realized by the invention over the prior art.

It is a primary object of the present invention to provide an endoscopic probe apparatus having a tube with multi-lumens, one of which provides a passage through which the irrigation and suction can occur and the other to provide passage for an electro-surgical cutting tip slidably extendable and retractable therethrough.

It is another primary object of the present invention to provide an endoscopic probe apparatus having a multiplicity of functions such as: the application of a negative pressure and an irrigation stream to the operative site; the application of an electric voltage to the surgical tip to simultaneously cut and cauterize the tissue in contact therewith; extending and retracting the surgical tip relative to the distal end of the multi-lumen tube; and rotating the multi-lumen tube and surgical tip relative to the probe handle.

It is another primary object of the present invention to provide an endoscopic probe apparatus having a plurality of controls conveniently positioned on the probe handle so as to enable the selective operation of the multiplicity of probe functions by a single hand thereby freeing the surgeon's second hand for other functions.

It is yet another object of the present invention to provide a probe apparatus having a multi-lumen tube with a minimum outside diameter so as to fit through a minimum size opening made through the patient, and which has an overall useable bore length sufficient to reach down through a trocar bore to the surgical site.

It is an associated object of the present invention is to provide a multi-functional endoscopic probe apparatus that is, in part, of light-weight molded acrylic construction, economical to manufacture, and that is entirely disposable after a single use.

These and other objects and features of the present invention will become more fully apparent from the following description and appended claims taken in conjunction with the accompanying drawings, or may be learned by the practice of this invention. Additional objects and advantages of the invention will be set forth in the description which follows, and in part will be obvious from the description, or may be learned by the practice of the invention.

Briefly summarized and to achieve the foregoing objects in accordance with the present invention as embodied and broadly described herein, a multi-functional endoscopic probe apparatus is provided. The probe apparatus comprises an elongated multi-lumen tube having a first lumen for the passage of either a high and low pressure irrigation stream therethrough, a second lumen for suction to remove excess fluid and debris, and a third lumen for the passage of a slidably extendable and retractable electro-surgical cutting tip. The multi-lumen probe is attached to a pistol grip configured to enable the multiplicity of functions to be conveniently and operatively controlled therefrom by a single hand.

The pistol grip handle has a wheel which enables the surgeon to rotate the multi-lumen tube containing the surgical cutting tip relative to the pistol grip. A plurality of push-button valves enable the selective application of negative pressure for withdrawing excess fluids and removing incident tissue debris from the surgical site and to operatively apply a flood irrigation stream or a precise irrigation stream to the surgical site to wash and cleanse the tissue. An multi-position electric switch directs either a low or a high frequency voltage to an electro-surgical cutting tip in order to cut and cauterized the tissue in contact therewith.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered limiting of its scope, the invention will be described and explained with additional specificity and detail through the use of the accompanying drawings in which:

FIG. 9 is a cross-section of the preferred multi-lumen embodiment of FIG. 5 as per the 9—9 line, further illustrating the larger semi-circular lumen for high volume low velocity irrigation fluid to pass therethrough and through which suction is drawn, a rectangular lumen for the slidable extension and retraction of the cutting tip, and a smaller lumen for low volume high velocity irrigation fluid to pass through.

DETAILED DESCRIPTION OF THE PREFERRED EMBODIMENTS

Reference is now made to the drawings wherein like parts are designated with like numerals throughout.

Figure 1:
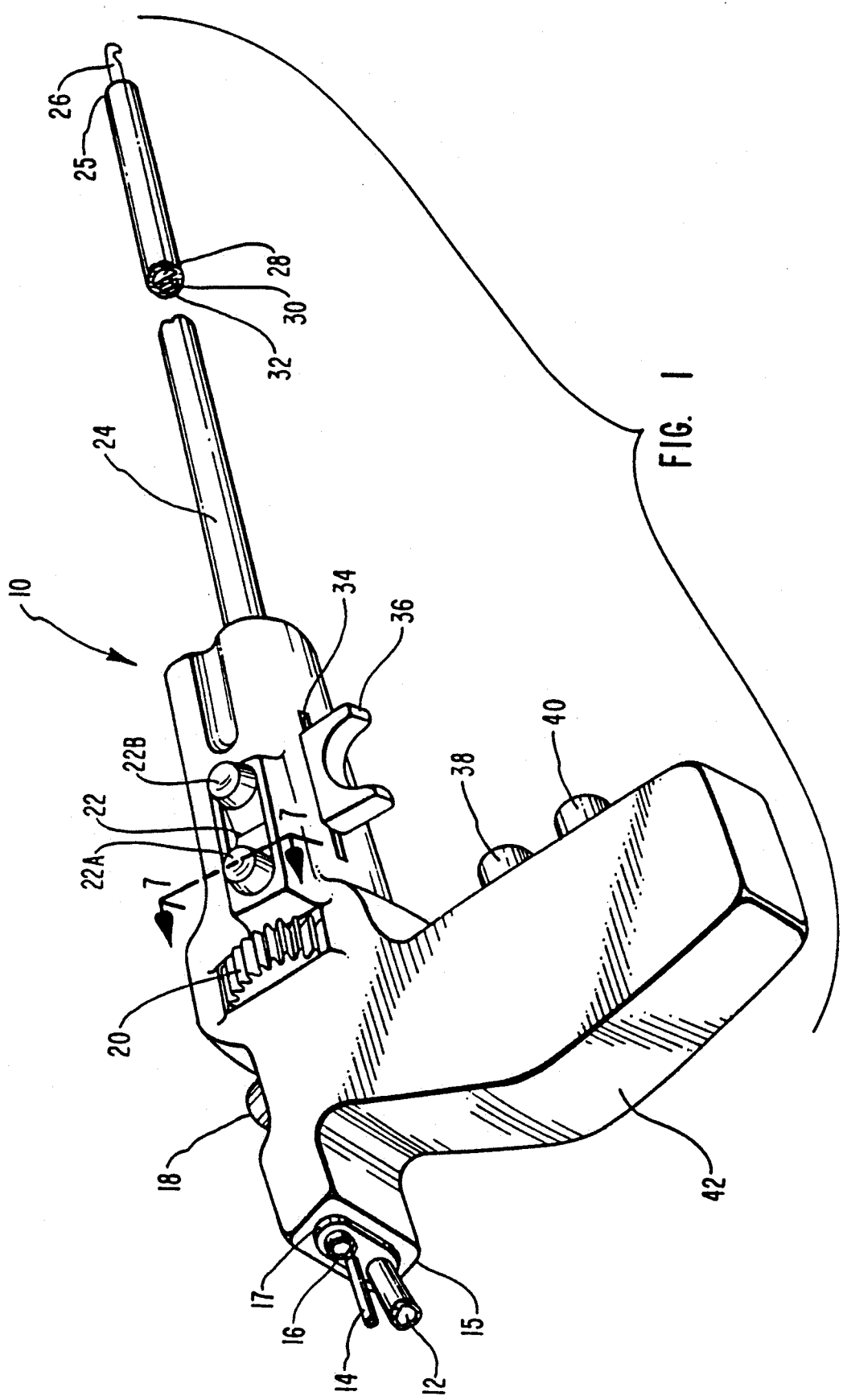
FIG. 1 is a top perspective view of the preferred embodiment of the present invention illustrating the pistol grip having a trigger for extending and retracting the cutting tip, an electric switch for the operations that cut and cauterize, a wheel for rotating the cutting tip relative to the pistol grip, and a plurality of push-button valves for suction and high and low irrigation streams.

FIG. 1 provides a top perspective view of the preferred embodiment of the present invention and, illustrates the multi-functional endoscopic probe apparatus, generally designated at 10, having a proximal end 15 and a distal end 25 thereof. In the preferred embodiment, a handle means comprises a pistol grip 42 to easily conform to the shape of the human hand, the use of which is further illustrated in FIGS. 2-4 and 10 to be discussed herein. An elongated multi-lumen tube 24, having a triple lumen configuration, designated as 28, 30 and 32, is attached to the pistol grip 42 enabling the probe apparatus 10 to be conveniently held and operatively controlled with one hand as to the plurality of functions provided thereon. At the distal end 25 of the multi-lumen tube 24, an electro-surgical tip 26 is secured for selective electro-surgical cut and/or cautery. The tip 26 is selectively extendable and retractable by trigger 36 slidable through and along trigger slot 34.

Extending past and secured through a proximal end 15 of the probe apparatus 10 by end plug 17 are suction and irrigation hoses, at 12 and 16 respectively, and electrocautery cable 14. Suction hose 12 connects to a source of negative pressure, not shown, the flow of which is operatively controlled by a suction push-button valve 18 such that fluids and debris can be siphoned away from the operative site when needed to clear the field of vision. A single irrigation hose 16 connects to a source of positive fluid pressure, not shown, entering the proximal end 15 of the pistol grip 42 to be separated into two distinct irrigation hoses, 39 and 41, (see FIGS. 5 and 6) by a Y-connector reference number 43, so as to provide the probe apparatus 10 with flood and precise irrigation streams the flow of which are operatively controlled by a pair of high and low irrigation push-button valves, designated as 38 and 40 respectively. Electro-cautery cable 14, which connects through the two wires shown in FIGS. 3-5 to a source of high and low frequency voltage not shown, electrically communicates with the electro-surgical tip 26 through a dual function electric switch 22 positioned on a side of the pistol grip 42 and, by way of example, having a first switch position to enable a high frequency voltage to the electro-surgical tip 26 and a second switch position to enable a low frequency voltage source to the tip. Wheel 20 enables the professional to change the relative position of the multi-lumen tube 24 with respect to the pistol grip 42 in a continuous 360 degree rotation while maintaining active use of one or more of the plurality of functions provided by the multi-functional probe apparatus 10 through the multi-lumen tube 24.

The handle means of the preferred embodiment comprises a pistol grip 42 constructed of a relatively resilient, non-toxic plastic material commonly found in the arts which can be molded so as to secure the internal components which provide the multiplicity of functions of the probe apparatus 10 therein. The pistol grip has an overall length in the range of from about 5 to 6 inches so as to conform to a normal sized hand, although larger and smaller pistol grips are contemplated. The presently illustrated pistol design is preferred and the multiplicity of functions conveniently located thereon so as to enable the entire probe apparatus 10 to be conveniently and operatively controlled by a single hand. It is to be understood and appreciated that the stated handle means could be designed in a variety of different ways while still enabling substantially the same set or subset of probe apparatus functions as discussed herein, and that such variations are therefore intended to be within the scope of the invention.

Figure 5:
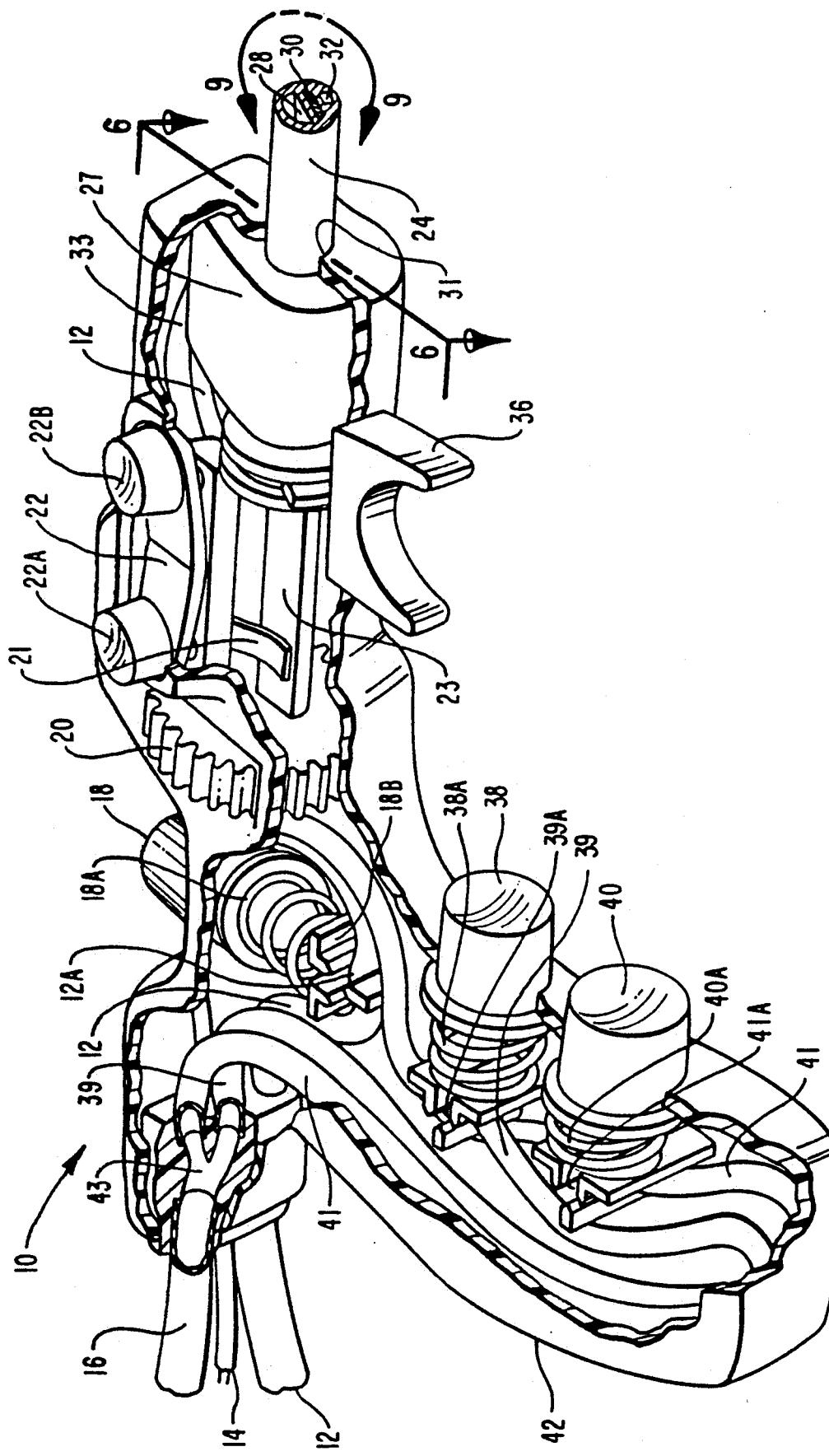
FIG. 5 is a top perspective view of the probe apparatus of the present invention broken away to illustrate the arrangement of the internal components of the pistol grip.
Figure 6:
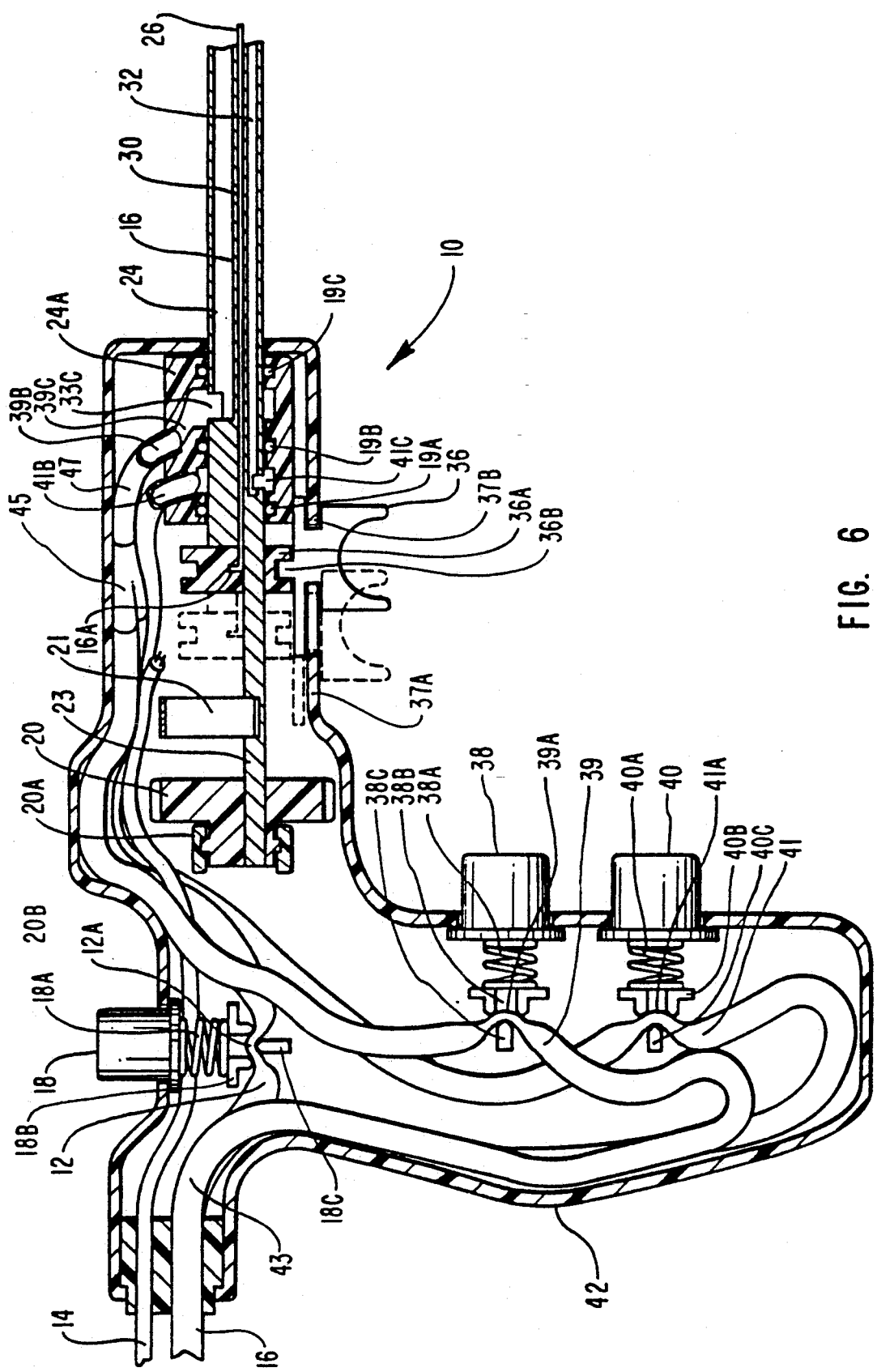
FIG. 6 is a longitudinal section of the probe apparatus of the present invention further illustrating the multi-lumen tube and the arrangement of the electrical components of the pistol grip.

With reference to FIG. 5, the multi-lumen tube 24 passes through a circular opening 31 made through the distal end of the pistol grip 42 and is secured to the pistol grip 42 by rotational and slidable engagement with securing block 27 affixed therein. In the present embodiment, the securing block 27 comprises a dual inner chamber configuration each of which are in communication with one or more suction and irrigation hoses, as shown in FIG. 6 and more thoroughly discussed herein.

Figure 9:
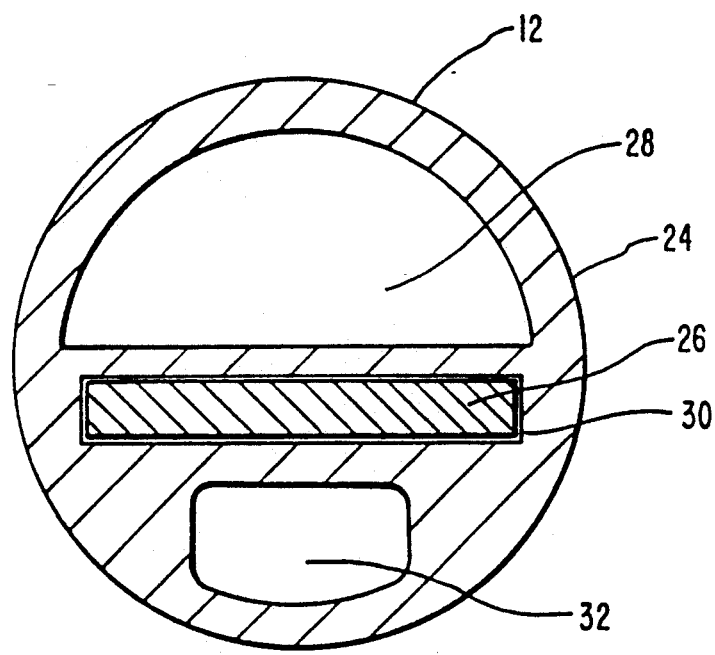

With reference being made now to FIG. 9, the presently preferred embodiment of the multi-lumen tube 24 comprises a triple lumen. A substantially rectangular first lumen 30 provides passage for the slidable extension and retraction of the electro-surgical tip 26. A larger substantially semicircular second lumen 28 provides a passageway for a relatively high volume, low velocity or "flood" irrigation stream therethrough. Additionally, the second lumen 28 provides a passageway through which suction can be drawn in order to remove unwanted fluid and debris from the operative site. A relatively smaller third lumen 32 provides a passageway for a relatively low volume, high velocity or "precise" irrigation stream which can be directed to a specific area to wash away blood or tissue occluding the surgeon's view of the operative site. Although the multi-lumen tube of the present invention is of triple lumen construction, it is to be understood that any combination of lumens and functions, such as, by way of example and not limitation, a single lumen through which all irrigation, suction, and cut/cauterize functions are performed or a plurality of lumens through which various combinations of irrigation, suction, and cut/cauterize functions are performed, is contemplated by the present invention and therefore to be considered in all respects another embodiment within the scope of the present invention.

Preferably, the inner and outer surfaces of the multi-lumen tube 24 have a polyamide coating of uniform thickness. A polyamide coating is desireable as an insulation coating for the multi-lumen tube of the multi-functional probe apparatus of the present invention because a polyamide coating has a relatively high dielectric strength, (i.e., the capacity to electrically insulate or shield one conductive surface from another), at relatively small thicknesses. The polyamide coating effectively insulates in coating thicknesses which are thin enough so as not to significantly reduce the overall inside bore diameter of the lumens over which the polyamide coating is applied while providing high dielectric properties to the metallic surfaces thereof. In addition, the polyamide coating has the further capacity to effectively prevent the leaching of toxic metallic ions from the metallic surfaces of the multi-lumens into the patient by way of the irrigation streams passing in contact therewith.

The presently preferred embodiment of the multi-lumen tube 24 comprises a highly conductive extruded aluminum tube, or in an alternative embodiment contemplated, the outer sheath of the multi-lumen tube 24 comprises a conductive stainless steel metal having an extruded plastic polymer insert secured within the bore of each lumen. In either embodiment, one can appreciate that during the application of a voltage source to the electro-surgical tip 26, when there is a substantial high or low frequency voltage passing through the conductive multi-lumen tube 24, surrounding tissue will most likely be in contact with the outer surface of the multi-lumen tube 24. In order to provide additional insulation protection to the surrounding tissue against inadvertent contact with this electric voltage passing through the tube, the outer surface of the tube is further coated with a shrink-wrapped polytetraflouroethylene layer which serves to effectively increase the overall dielectric strength of the uniform polyamide coating layer. The application of a uniform layer of shrink-wrap coating to the outer surface of the multi-lumen tube gives the tube an overall uniform outside diameter in the range of from about 5 mm to 7 mm in thickness.

Figure 10:
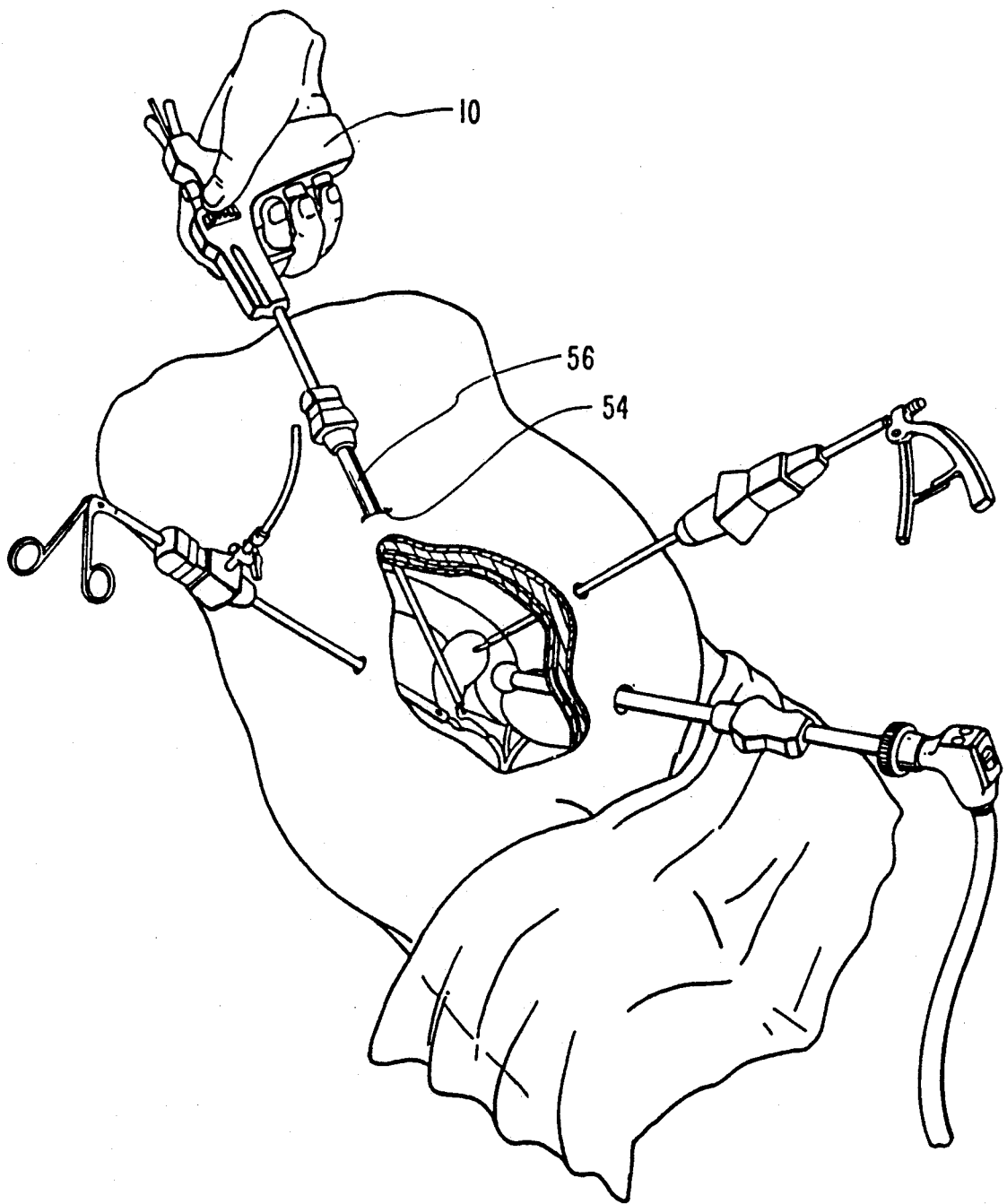
FIG. 10 is a perspective view of the probe apparatus of the present invention wherein the elongated multi-lumen tube is positioned through one of four trocar devices in order to perform a surgical procedure therethrough.

The multi-lumen tube 24 of the preferred embodiment slightly tapers from the proximal end 15 to the distal end 25 of the probe apparatus 10. Such a tapered configuration of the multi-lumen tube, in conjunction with the minimal overall uniform outside diameter discussed above, facilitates the insertion of the multi-lumen tube down the bore of a trocar device 56 which has been inserted through an incision in the patient 54, as shown in FIG. 10. Further, the multi-lumen tube 24 has an overall length of from about 30 cm. to about 32 cm measured from the most distal end of the tube 24 to the most proximal end of the multi-lumen tube. The above-describe overall length of the tube is to be considered in all respects illustrative and not limiting in the scope of the present invention.

One could appreciate the need for a multi-functional probe apparatus having a different overall tube length. For example, one surgical procedure might require the use of the multi-functional probe apparatus through one of the patient's bodily orifices because the surgical site can be easily and effectively reached through an orifice using a multi-function probe apparatus with a longer tube. In such an example and to meet the desired surgical objectives, the multi-functional probe apparatus would have to be constructed with a longer multi-lumen tube. It should be appreciated that in other contemplated embodiments of the present invention, the multi-lumen tube can be tailored as to the overall length of the tube so as to achieve each of a plurality of prescribed surgical modalities with respect to the procedures involved therein.

The endoscopic probe apparatus of the present invention advantageously provides a multiplicity of application functions in a single hand held apparatus, such as: first application means for applying a negative pressure to the lumen of the elongated tube; second application means for applying an irrigation stream to the lumen of the elongated tube; third application means for applying an electric voltage to the tip; fourth application means for extending and retracting the tip relative to the distal end of the elongated tube; and fifth application means for rotating the elongated tube and tip relative to the pistol grip. In order to achieve these application functions, the probe apparatus has a plurality of controls conveniently positioned on the pistol grip so as to enable the selective operation of each function alone or in combination by a single hand. Thus, as will be apparent from the drawings and the following description of the operative structures which provide each of the above functions, the endoscopic probe could be used to do any of the following single functions, in any order, or in the combinations which are mentioned below: rotating the cutting tip to any desired rotational orientation and then cutting and cauterizing tissue; suctioning smoke and/or tissue at the cutting site; irrigating the cutting site with either a small, high-velocity stream, or alternatively with a large, low velocity irrigation stream; or simultaneously irrigating with a small, high-velocity stream while at the same time applying suction.

With reference to FIG. 5, the probe apparatus 10 of the present invention comprises first application means for applying a negative pressure to one of the lumens of the multi-lumen tube wherein the first application means is connected to the second lumen 28 such that the negative pressure is selectively applied to the second lumen. In the preferred embodiment, the first control means for selectively operating the first application means is located on the pistol grip 42 and comprises a suction push-button valve 18, which is configured and located on a top side of the pistol grip 42 such that a thumb conveniently and operatively manipulates the push-button valve 18, as illustrate in FIG. 3.

With reference to FIG. 6, the push-button valve 18 is normally closed and permits the flow therethrough of the negative pressure only when pressed to an open position. To achieve the normally closed position of the suction push-button valve 18, the valve is normally biased by spring tension member 18A in order to keep a constant crimp in suction hose 12 at junction 12A. The spring biasing of the suction push-button valve 18 is effectively enabled by the compression of spring tension member 18A between the bottom edge of the push-button 18, which is secured in place by the casing of the pistol grip 42, and the pair of stationary spring butts, both designated as 18B. In the normally closed position, it should be appreciated that no suction is drawn through suction hose 12 because, at junction 12A, the tension of member 18B between the stationary spring butts 18B and the bottom of the push-button 18 drives slidable wedge 18C between the spring butts and effectively crimps hose 12 at that point. In order to draw a suction through suction hose 12 such that the fluids and debris at the operative site can be effectively and efficiently withdrawn, suction push-button valve 18 is pressed to release the spring biasing thereunder and release wedge 18C from its secure lock on hose 12.

One should appreciate that in order to effectuate the complete closure of the hose at the junction point, the hose must be constructed of a durable flexible material of sufficient structural integrity so as to withstand the constant crimping and releasing at a single junction point while not rupturing under the pressure contained therein. In the preferred embodiment, the hoses are of a medical grade plastic tubing that can withstand a plurality of sterilization techniques while retaining sufficient structural integrity. Further, one can appreciate that the crimping edge of each slidable wedge 18C should be sharp enough so as to effectuate complete closure of the hose at the particular junction while not cutting through the wall of the hose at that junction. In addition, the biasing of the respective spring tension member should be sufficient so as to effectively pressure the respective slidable wedges into closure of the hose at the junction point without driving the crimping edge of wedge through the wall of the hose. It should be appreciated that a rupture of either a suction hose or an irrigation hose during a surgical procedure could result in the complete loss of that specific function which may adversely affect the surgical procedure and ultimately the patient's health.

Figure 4:
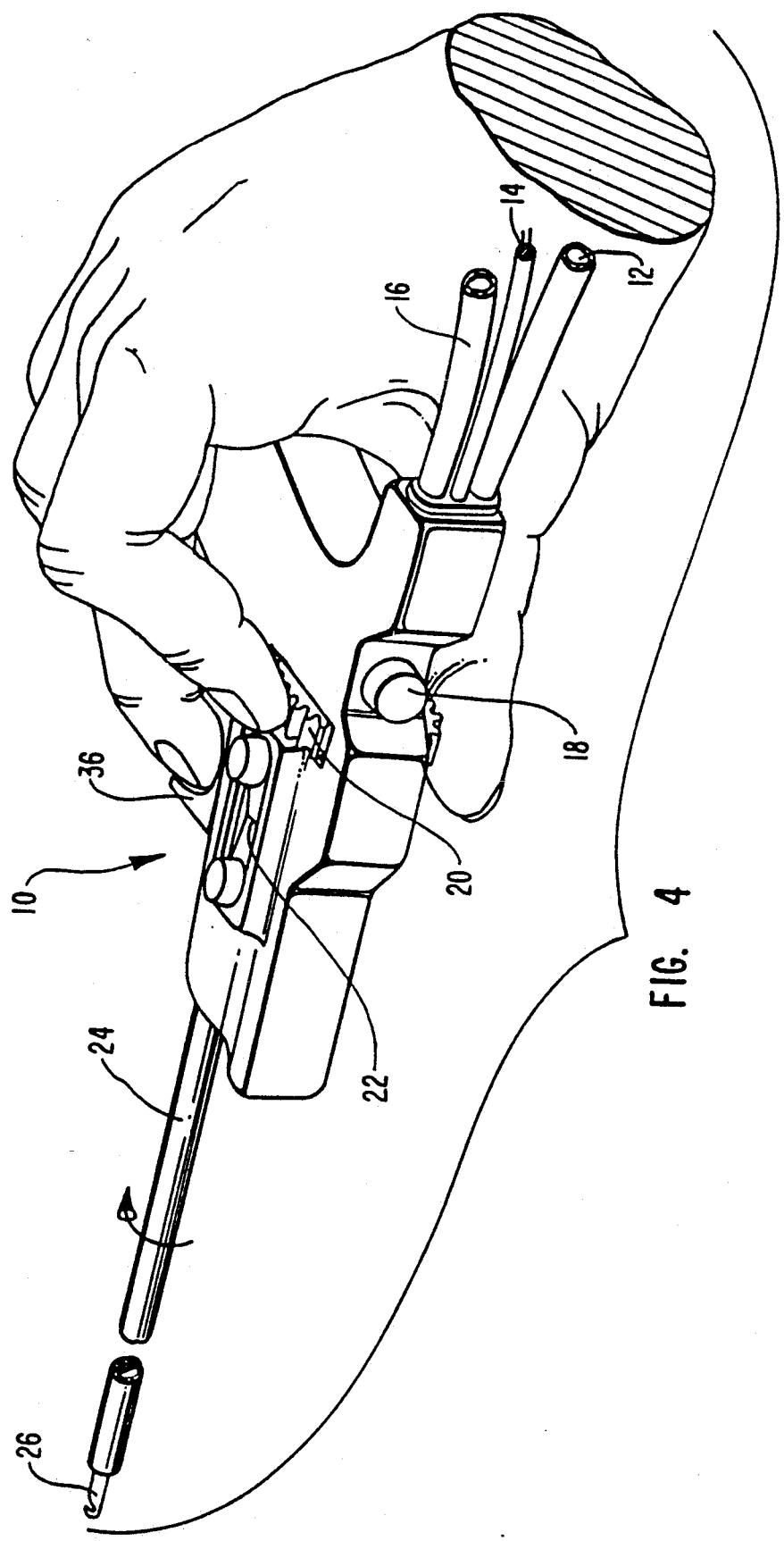
FIG. 4 is a top perspective view of the probe apparatus held in the right hand, more particularly illustrating the thumb and index finger selectively rotating the wheel in order to rotate the multi-lumen tube and the cutting tip relative to the pistol grip, and selectively extending or retracting the cutting tip.

With reference to FIG. 6, the probe apparatus 10 of the present invention further comprises second application means connected to the second lumen 28 such that the fluid flow therethrough is selectively applied to the second lumen. The present embodiment further comprises second control means for selectively operating the second application means and comprising first means for directing fluid flow to the second lumen 28, and second means for directing fluid flow to the third lumen 32. In the present embodiment, the first means for directing fluid flow to the second lumen 28 comprises a flood irrigation push-button valve 38 and the second means for directing a fluid flow to the third lumen 32 comprises a precise irrigation push-button valve 40. The pair of irrigation push-button valves, at 38 and 40, are located on a distal side of the pistol grip 42 and function to regulate the fluid flow through flood and precise irrigation hoses, 39 and 41 respectively. The single incoming irrigation hose 16 is split into a pair of irrigation hoses 39 and 41 such that each respective irrigation hose can be operatively controlled through the spring biasing of each individual push-button valve, which as shown in FIG. 4, are configured and located on the pistol grip 42 such that a ring finger and a little finger conveniently and operatively manipulate the respective irrigation functions.

With reference to FIG. 6, and in a manner similar to that of the configuration of the spring biased suction push-button valve 18 discussed above, flood irrigation push-button valve 38 is spring biased by spring tension member 38A so as to maintain a crimp in flood irrigation hose 39 at junction 39A. The spring biasing of the flood irrigation push-button valve 38 is effectively enabled by the compression of spring tension member 39A between the bottom edge of the push-button 38, which is secured in place by the casing of the pistol grip 42, and the pair of stationary spring butts, both designated as 38B. In the normally closed position, no flood irrigation passes through flood irrigation hose 39 because, at junction 39A, the tension of member 38A between the stationary spring butts 38B and the bottom of the flood irrigation push-button 38 drives slidable wedge 38C between the spring butts and effectively crimps flood irrigation hose 39 at that point. In order to allow an irrigation fluid to flow through flood irrigation hose 39 to wash the operative site, flood irrigation push-button valve 38 is pressed to release the spring biasing thereunder and release wedge 38C from its secure lock on the flood irrigation hose.

Similarly, precise irrigation push-button valve 40 is spring biased by spring member 40A to maintain a crimp in precise irrigation hose 41 at junction 41A. In the normally closed position, no precise irrigation passes through precise irrigation hose 41 because, at junction 41A, the tension of member 40A between the stationary spring butts 40B and the bottom of the precise irrigation push-button valve 40 drives slidable wedge 40C between the spring butts and effectively crimps precise irrigation hose 41 at that point. In a manner similar to the suction and the flood irrigation push-button valves, in order to allow an irrigation fluid to flow through the precise irrigation hose 41, push-button valve 40 is pressed to release the spring biasing thereunder.

At the distal end of the pistol grip 42, flood irrigation hose 39 is joined with suction hose 12 by Y-connector 45 which forms single hose 47 sealingly attached at connection 39B to annulus chamber 39C. The connection of single hose 47 at 39B places the flood irrigation source in communication with annulus chamber 39C formed within securing block 27. In the present embodiment, O-rings 19B and 19C effectively seal both sides of annulus chamber 39C so as to insure airtight communication between hose 47 and second lumen 28 of the multi-lumen tube 24. Such an annulus configuration enables a flood irrigation stream to pass therethrough to the second lumen 28 independent of the rotational positioning of the multi-lumen tube 24 by ridged wheel 20.

In a similar manner, precise irrigation hose 41 is sealingly attached at connection 41B to annulus chamber 41C. The connection of hose 41 at 41B places the precise irrigation source in communication with annulus chamber 41C formed within securing block 27. In the present embodiment, O-rings 19A and 19B effectively seal both sides of annulus chamber 41C so as to insure airtight communication between hose 41 and first lumen 32 of the multi-lumen tube 24. Such an annulus configuration enables a precise irrigation stream to pass therethrough to the first lumen 32 independent of the rotational positioning of the multi-lumen tube 24 by ridged wheel 20. Since in the present embodiment the single irrigation line 16 is connected to a pressurized source of irrigation fluid, the passage of the irrigation fluid from the annulus chamber into the smaller inner diameter first lumen 32 increases the pressure therein forcing a fine stream of irrigation fluid out the distal end of the multi-lumen tube.

The probe apparatus 10 of the present invention further comprises third application means for applying an electric voltage to the electro-surgical tip 26 and comprises third control means for selectively operating the third application means. In the preferred embodiment, the third control means comprises an electric switch 22 having a first position 22A, for example, to enable a high frequency voltage to the electro-surgical tip 26 and second position 22B to enable a low frequency voltage source to the tip.

Figure 7:
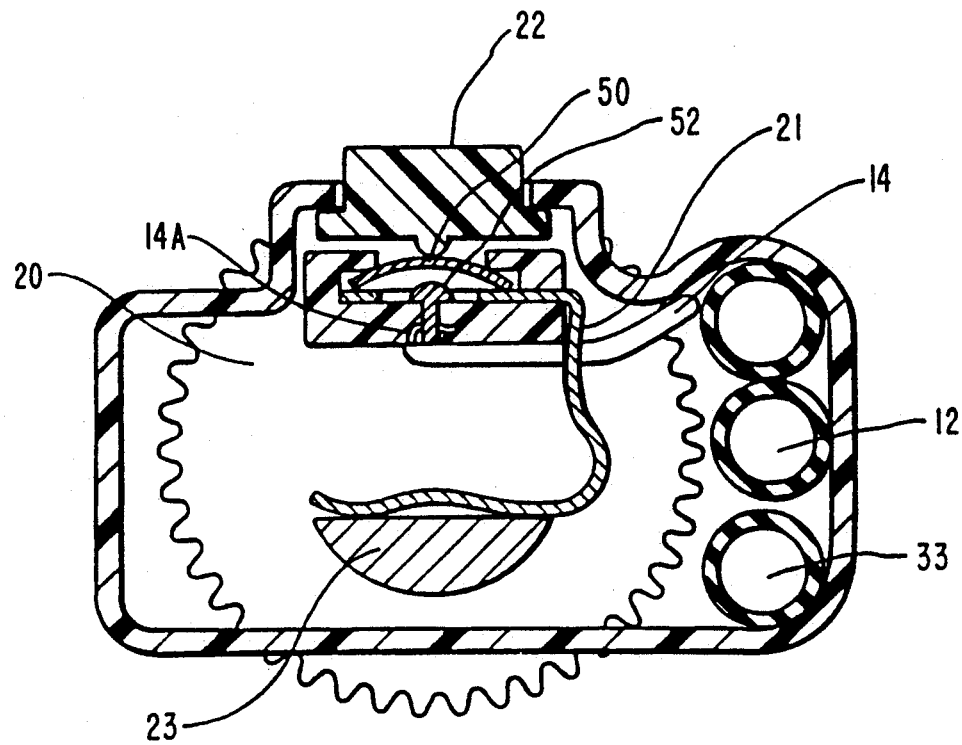
FIG. 7 is a cross-sectional view of the electric switch of FIG. 1 in the "OFF" position.
Figure 8:
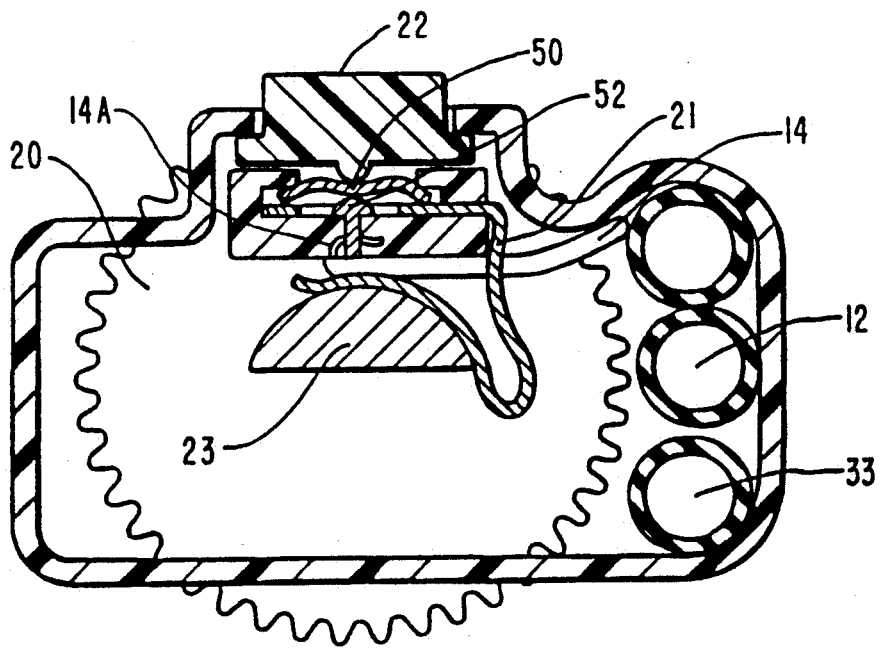
FIG. 8 is a cross-sectional view of the electric switch of FIG. 1 in the "ON" position connecting either a high or low frequency voltage source to the cutting tip.

With reference now to FIGS. 5, 7 and 8 collectively, cable 14 electrically connects to hook 14A in electrical communication with pin 52 located just under bridge member 50 positioned directly beneath the switch 22. Specifically, FIG. 7 illustrates the switch 22 in the "OFF" position, wherein hook 14A and pin 52 are not in electrical communication with bridge member 50. FIG. 8 illustrates the switch 22 in the "ON" position, wherein hook 14A and pin 52 are in electrical communication with bridge member 50. As shown in FIG. 8, when the switch 22 is pressed the bridge member 50 is placed in direct electrical contact with pin 52. The contact of the bridge member 50 and pin 52 establishes electrical communication with the voltage source, not shown, through contact with contact flange 21, which is in constant physical contact with flat tube end 23 of the multi-lumen tube 24, which in turn is in constant electrical contact with electro-surgical tip 26. As ridged wheel 20 is circumferentially rotated in conjunction with the pressing of the electric switch 22 to effectuate the closure of bridge member 50 and pin 52, contact flange 21 provides electrical communication with the tip 26.

Figure 3:
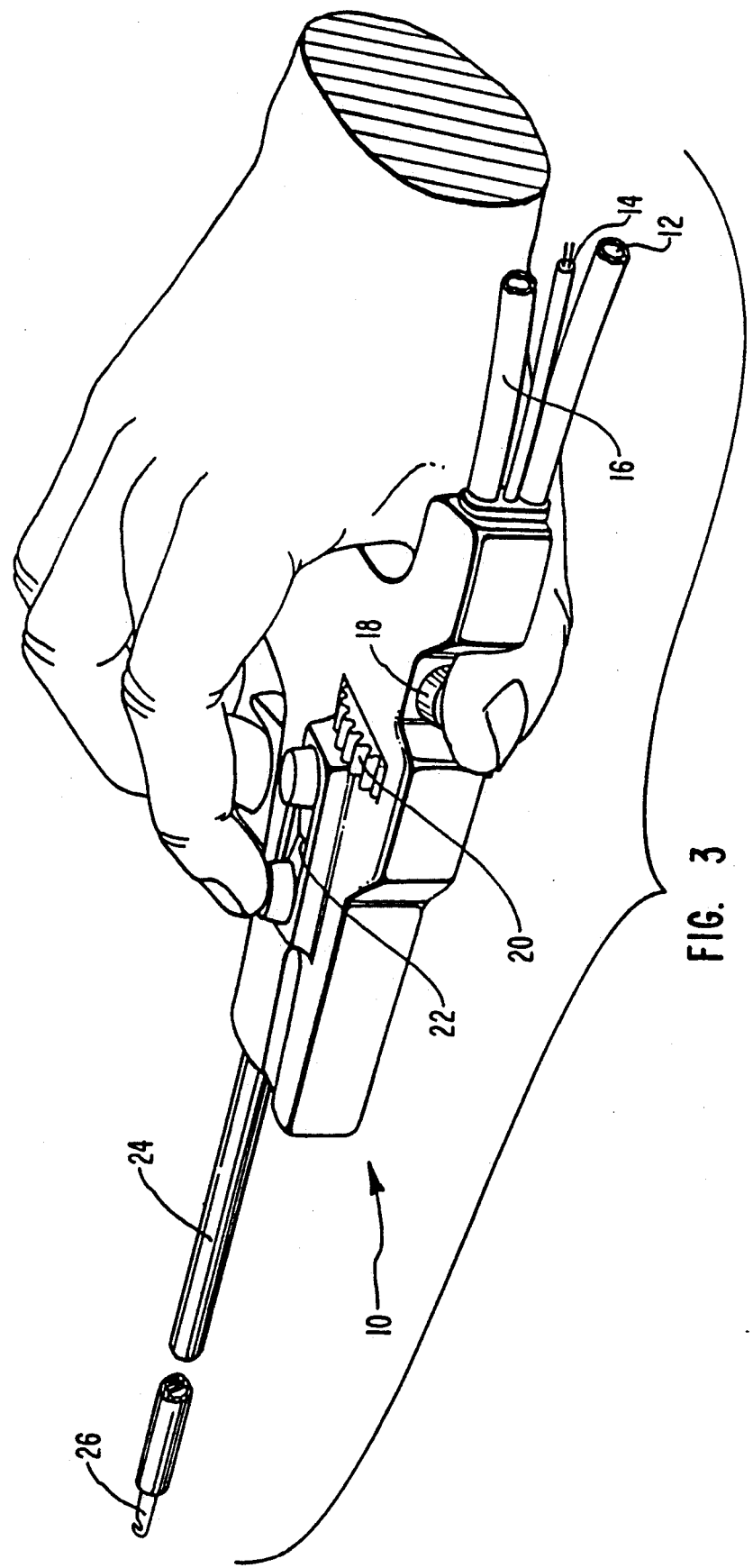
FIG. 3 is a top perspective view of the probe apparatus held in the right hand, illustrating the thumb manipulating a push-button valve to apply suction through the multi-lumen tube, the index finger on the electric switch selecting either a high or low frequency voltage to perform the cut and cauterize functions, and the middle finger in the trigger position extending or retracting the cutting tip.

With reference to FIG. 3, the electric switch 22 is located on a side of the pistol grip such that an index finger conveniently and operatively manipulates the application of the electrical voltage source to the electro-surgical tip 26. In such a manner, the medical professional can apply either a high or low frequency electric voltage to the electro-surgical tip 26 while rotating the multi-lumen tube 24 in a 360 degree continuous rotation and still perform cut or cautery.

The probe apparatus 10 of the present invention comprises fourth application means for extending and retracting the electro-surgical tip 26 relative to the distal end of the multi-lumen tube 224 and comprises fourth control means for operating the fourth application means for extending and retracting the tip. In the presently preferred embodiment, fourth the control means advantageously comprises a trigger 36, selectively slidable along and through trigger slot 34, and shaped to allow a finger to easily extend and retract the electro-surgical tip 26. With reference to FIG. 6, trigger 36 engages flange 36A by trigger tab 36B through trigger slot 34. The flange 36A engages the tab 16A so as to secure the trigger 36 to the most proximal end of the cutting tip 26. With such a configuration, the electro-surgical tip 26 can be selectively extended by the forward motion of the trigger 36 toward the distal end 25 of the probe apparatus 10 and positioned out past the most distal end of the multi-lumen tube 24 up to the full extension. The forward motion of the trigger 36 is terminated by reaching trigger stop 37B at the distal end of trigger slot 34. By the backward motion of the trigger 36 towards the proximal end 15 of the probe apparatus 10, the electro-surgical tip 26 can be retracted the desired amount in order to achieve the desired positioning. The backward motion of the trigger 36 along trigger slot 34 is terminated by hitting the trigger stop 37A.

FIG. 4 illustrates the probe apparatus 10 held in the right hand wherein the middle finger is positioned on the trigger 36 to extend and retract the electro-surgical tip 26. In the present embodiment, the tip can preferably be extended from between 5 mm to 7 mm beyond the most distal end 25 of the multi-lumen tube 24 of the probe apparatus, preferably extending in the range of from about 6 mm to 8 mm past the most distal end of the multi-lumen tube so as to effectively reach the tissue to be cut and/or cauterized. Of course, other such extending ranges are possible without exceeding the scope of the present invention and are herein contemplated as being within the scope to the present invention.

The probe apparatus of the present invention further comprises fifth application means for rotating the multi-lumen tube and tip relative to the handle means and comprises fifth control means for operating the fifth application means. In the preferred embodiment, the fifth control means comprises a splined wheel 20, which extends through the pistol grip 42 to facilitate manipulation. With reference being made now to FIG. 6, the wheel 20 is secured to an internal portion of pistol grip 42 by wheel securing member 20A engaging the wheel 20 by circumferential wheel tabs 20B which permit the rotation of the wheel 20 relative to the pistol grip. As shown in FIGS. 5 and 6, the wheel 20 has a semi-circular slot slidably receiving therethrough flat tube end 23 of the multi-lumen tube 24.

Figure 2:
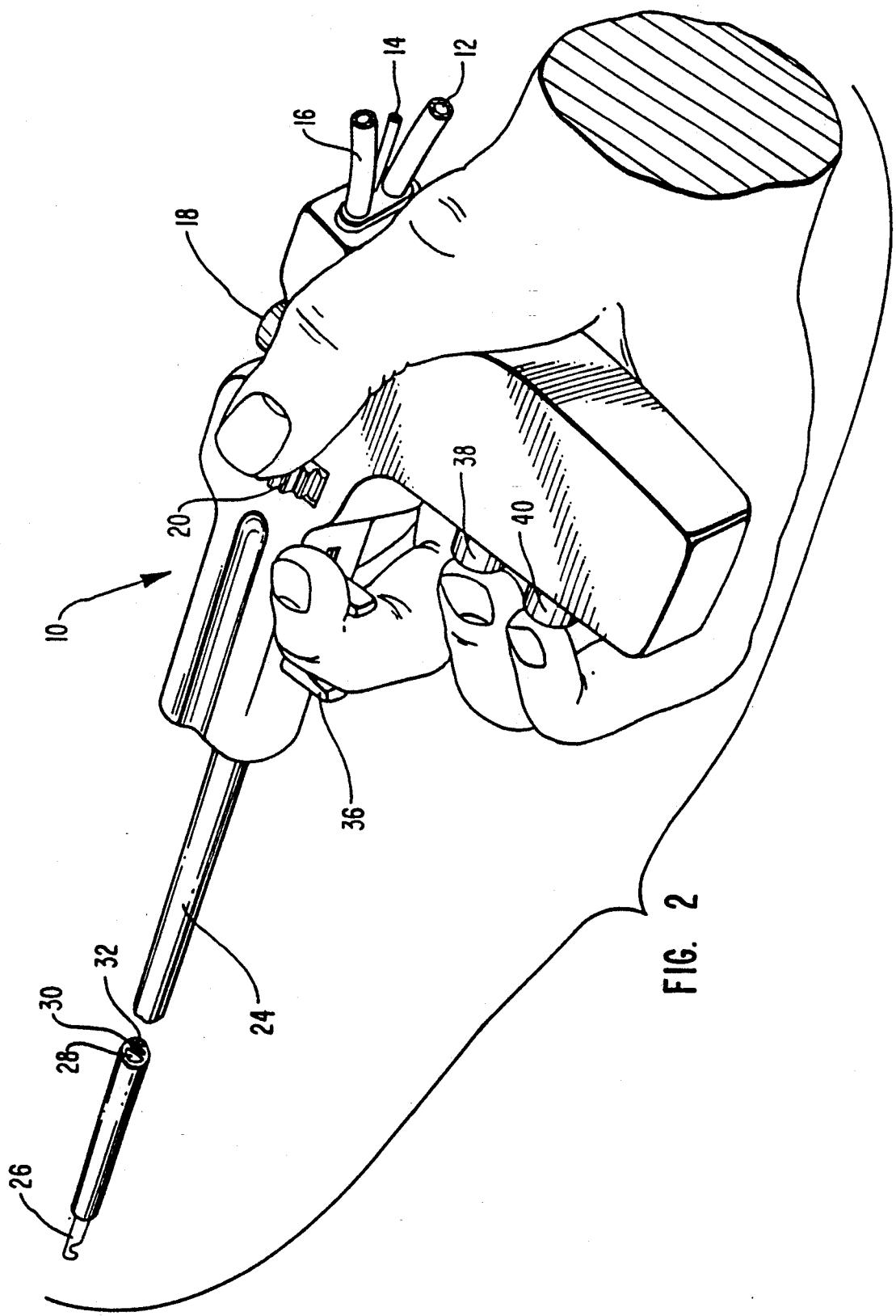
FIG. 2 is a bottom perspective view of the probe apparatus held in the right hand, illustrating the thumb manipulating the wheel in order to rotate the cutting tip relative to the piston grip, the middle finger on the trigger to extend and retract and cutting tip, and the ring and little fingers selectively applying a floor irrigation and/or a precise irrigation stream.

With reference to FIG. 2, which is a top perspective view of the probe apparatus 10 held in the right hand, the wheel 20 is located on a forward side of the pistol grip such that the thumb and index finger selectively rotate the wheel 20. By the selective rotation of the wheel 20 relative to the pistol grip 42, the professional can change the relative positions of the multi-lumen tube 24 with respect to the pistol grip 42 in a continuous 360 degree rotation while maintaining the functions applied therethrough so as to orient the hooked end 26 as desired.

FIG. 10 is a perspective view of the probe apparatus of the present invention wherein the elongated multi-lumen tube is positioned to one of four trocar devices in order to perform a surgical procedure therethrough. FIG. 10 thus illustrates in an exemplary way one way in which the multi-lumen endoscopic probe apparatus 10 of the present invention may be employed in the context of an endoscopical surgical procedure.

It is to be understood and appreciated that each of the stated means could be designed in a variety of different ways while still performing the same functions as described by way of illustration with respect to each such means, and such variations are therefore intended to be within the scope of the invention as broadly described and claimed herein. It should be further understood that although the use of the endoscopic probe apparatus of the present invention is disclosed with respect to use in laparoscopic cholecystectomy, it is the intent that the present invention find uses as a multi-functional endoscopic probe apparatus in a wide variety of endoscopic procedures including but not limited to appendectomies, hernias, hiatal hernia repair, ablation of endometriosis, retro-ectopic pregnancies, adhesions, and abdominal adhesions.

The present invention may be embodied in other specific forms without departing from the spirit of this invention or its essential characteristics. The described embodiments are to be considered, in all respects, as illustrative and not restrictive. The scope of the invention is, therefore, indicated by the appended claims rather than by the foregoing description. All changes which come within the meaning and range of equivalency of the foregoing claims are to be embraced within their scope.

What is claimed and desired to be secured by United States Letters Patent is:

1. A multi-functional endoscopic probe apparatus comprising:

an elongated tube comprising a lumen therethrough and an electro-surgical tip means for the selective electro-surgical cutting and cauterizing at a distal end of said elongated tube wherein said tube is comprised of multiple lumens therethrough and wherein said electro-surgical tip means comprises an elongated metallic member slidably situated in a first lumen;

first application means for applying a negative pressure to one of the lumens of said elongated tube;

second application means for applying an irrigation stream to one of the lumens of said elongated tube;

third application means for applying an electric voltage to said tip means; and handle means for enabling said apparatus to be conveniently held and operatively controlled with one hand as to all functions provided by each of said application means, said handle means attached to a proximal end of said elongated tube and wherein said handle means comprises:

first control means for selectively operating said first application means;

second control means for selectively operating said second application means; and third control means for selectively operating said third application means; and wherein said second control means comprises first means for directing fluid flow to a second lumen, and second means for directing fluid flow to a third lumen, and wherein said third lumen is substantially smaller in cross-sectional area than said second lumen such that a relatively small, high velocity irrigation stream is provided through said third lumen, and a relatively large, low velocity irrigation stream is provided through said second lumen.

2. An apparatus as defined in claim 1, further comprising:
fourth application means for extending and retracting said tip means relative to the distal end of said elongated tube;
fifth application means for rotating said elongated tube and tip means relative to said handle means.

3. An apparatus as defined in claims 1 or 2, wherein said third control means comprises first means for the application of a voltage at a first frequency such that sufficient electrical energy is provided at said tip means for cutting tissue, and second means for the application of a voltage at a second frequency such that sufficient electrical energy is provided at said tip means for cauterizing tissue.

4. An apparatus as defined in claim 2, wherein said handle means comprises:
fourth control means for operating said fourth application means; and
fifth control means for operating said fifth application means.

5. An apparatus as defined in claim 4, wherein said handle means further comprises a pistol grip.

6. An apparatus as defined in claim 5,
wherein said first control means is located on said pistol grip, and
wherein said second control means is located on said pistol grip, and
wherein said third control means is located on said pistol grip, and
wherein said fourth control means is located on said pistol grip, and
wherein said fifth control means is located on said pistol grip.

7. An apparatus as defined in claim 6, wherein said first control means comprises a suction push-button valve that is normally closed and permits the flow therethrough of said negative pressure when pressed to an open position.

8. An apparatus as defined in claim 6, wherein said third control means comprises an electric rocker switch having at least two positions for directing a high and low frequency voltage to said tip means.

9. An apparatus as defined in claim 6, wherein said fourth control means comprises a slidable blade-moving member extending through a slot in said pistol grip.

10. An apparatus as defined in claim 6, wherein said fifth control means comprises a blade-rotation member attached to a proximal end of said elongated tube so as to operatively turn said elongated tube and said tip means relative to said handle means.

11. An apparatus as defined in claim 1, wherein said first application means is connected to said second lumen such that the negative pressure is selectively applied to said second lumen.

12. An apparatus as defined in claim 11, wherein said third control means comprises first means for the application of a voltage at a first frequency such that sufficient electrical energy is provided at said tip means for cutting tissue, and second means for the application of a voltage at a second frequency such that sufficient electrical energy is provided at said tip means for cauterizing tissue.

13. An apparatus as defined in claim 11, wherein said second control means comprises first means for directing fluid flow to said second lumen, and second means for directing fluid flow to a third lumen, and wherein said third lumen is substantially smaller in cross-sectional area than said second lumen such that a relatively small, high velocity irrigation stream is provided through said third lumen, and a relatively large, low velocity irrigation stream is provided through said second lumen.

14. An apparatus as defined in claim 13, further comprising connector means for directing fluid flow, said connector means being responsive and selectively controlled at an outlet end thereof by one of said first control means and said first means for directing fluid flow, and said connector means being in fluid communication through an outlet end thereof with said second lumen.

15. An apparatus as defined in claims 1, wherein said third control means comprises first means for the application of a voltage at a first frequency such that sufficient electrical energy is provided at said tip means for cutting tissue, and second means for the application of a voltage at a second frequency such that sufficient electrical energy is provided at said tip means for cauterizing tissue.

16. An apparatus as defined in claim 1, wherein said first application means is connected to said second lumen such that the negative pressure is selectively applied to said second lumen.

17. An apparatus as defined in claim 16, wherein said second application means is connected to said second lumen such that the fluid flow therethrough is selectively applied to said second one of said lumens.

18. An apparatus as defined in claim 17, further comprising connector means for directing fluid flow, said connector means being responsive and selectively controlled at an outlet end thereof by one of said first application means and said means for directing fluid flow, and said connector means being in fluid communication through an outlet end thereof with said second lumen.

19. An apparatus as defined in claim 1, wherein said second application means is connected to said second lumen.

20. An apparatus as defined in claim 1, wherein said handle means further comprises a pistol grip.

21. An apparatus as defined in claim 20,
wherein said first control means is located on said pistol grip, and
wherein said second control means is located on said pistol grip, and
wherein said third control means is located on said pistol grip.

22. A multi-functional endoscopic probe apparatus comprising:
an elongated multi-lumen tube having at least first and second lumens therethrough and an electro-surgical tip comprising an elongated metallic member slidably situated in one of said lumens for the selective electro-surgical cutting and cauterizing at a distal end of said elongated tube;
first application means for applying a negative pressure to one of said lumens of said elongated tube;

second application means for applying an irrigation stream to one of said lumens of said elongated tube;

third application means for applying an electric voltage to said tip means;

fourth application means for extending and retracting said tip means relative to the distal end of said elongated tube;

fifth application means for rotating said elongated tube and tip means relative to said handle means; and handle means for enabling said apparatus to be conveniently held and operatively controlled with one hand as to all functions provided by each of said application means, said handle means attached to a proximal end of said elongated tube and wherein said handle means comprises:

first control means for selectively operating said first application means;

second control means for selectively operating said second application means;

third control means for selectively operating said third application means;

fourth control means for operating said fourth application means;

fifth control means for operating said fifth application means; and wherein said second control means comprises first means for directing fluid flow to said second lumen, and second means for directing fluid flow to a third lumen, and wherein said third lumen is substantially smaller in cross-sectional area than said second lumen such that a relatively small, high velocity irrigation stream is provided through said third lumen, and a relatively large, low velocity irrigation stream is provided through said second lumen.

23. An apparatus as defined in claim 22, wherein said first application means is connected to said second lumen such that the negative pressure is selectively applied to said second lumen.

24. An apparatus as defined in claim 23, further comprising connector means for directing fluid flow, said connector means being responsive and selectively controlled at an outlet end thereof by one of said first control means and said first means for directing fluid flow, and said connector means being in fluid communication through an outlet end thereof with said second lumen.

25. An apparatus as defined in claim 22, wherein said third control means comprises first means for the application of a voltage at a first frequency such that sufficient electrical energy is provided at said tip means for cutting tissue, and second means for the application of a voltage at a second frequency such that sufficient electrical energy is provided at said tip means for cauterizing tissue.

26. An apparatus as defined in claim 22, wherein said second application means is connected to said second lumen.

27. An apparatus as defined in claim 26, further comprising connector means for directing fluid flow, said connector means being responsive and selectively controlled at an outlet end thereof by one of said first application means and said means for directing fluid flow, and said connector means being in fluid communication through an outlet end thereof with said second lumen.

28. An apparatus as defined in claim 22, wherein said handle means further comprises a pistol grip, wherein said first control means is located on said piston grip, and wherein said second control means is located on said piston grip, and wherein said third control means is located on said piston grip, and wherein said fourth control means is located on said piston grip, and wherein said fifth control means is located on said piston grip.

29. An apparatus as defined in claim 22 wherein said first control means comprises a suction push-button valve that is normally closed and permits the flow therethrough of said negative pressure when pressed to an open position.

30. An apparatus as defined in claim 22, wherein said first control means comprises an irrigation push-button valve that is normally closed and permits the flow therethrough of said irrigation stream when pressed to an open position.

31. An apparatus as defined in claim 22, wherein said third control means comprises an electric rocker switch having at least two positions for directing a high and low frequency voltage to said tip means.

32. An apparatus as defined in claim 22, wherein said fourth control means comprises a slidable blade-moving member extending through a slot in said pistol grip.

33. An apparatus as defined in claim 22, wherein said fifth control means comprises a blade-rotation member attached to a proximal end of said elongated tube so as to operatively turn said elongated tube and said tip means relative to said handle means.

34. A multi-functional endoscopic probe apparatus comprising:

an elongated tube comprising a multi-lumen having at least first, second, and third lumens therethrough and an electro-surgical tip comprising an elongated metallic member slidably situated in one of said lumens for the selective electro-surgical cutting and cauterizing at a distal end of said elongated tube;

first application means for applying a negative pressure to said second lumen of said elongated tube and connected to said second lumen such that the negative pressure is selectively applied to said second lumen;

second application means for applying an irrigation stream to said first lumen of said elongated tube and connected to said second lumen such that the fluid flow therethrough is selectively applied to a second one of said lumens;

third application means for applying an electric voltage to said tip means;

fourth application means for extending and retracting said tip means relative to the distal end of said elongated tube;

fifth application means for rotating said elongated tube and tip means relative to said handle means; and handle means for enabling said apparatus to be conveniently held and operatively controlled with one hand as to the plurality of functions provided by each of said application means, said handle means attached to a proximal end of said elongated tube, said handle means comprising:

first control means for selectively operating said first application means;

second control means for selectively operating said second application means;

third control means for selectively operating said third application means;

fourth control means for operating said fourth application means; and fifth control means for operating said fifth application means; and wherein said second control means comprises first means for directing fluid flow to said second lumen, and second means for directing fluid flow to said third lumen.

35. An apparatus as defined in claim 34, further comprising connector means for directing fluid flow, said connector means being responsive and selectively controlled at an outlet end thereof by one of said first control means and said first means for directing fluid flow, and said connector means being in fluid communication through an outlet end thereof with said second lumen.

36. An apparatus as defined in claims 35, wherein said third control means comprises first means for the application of a voltage at a first frequency such that sufficient electrical energy is provided at said tip means for cutting tissue, and second means for the application of a voltage at a second frequency such that sufficient electrical energy is provided at said tip means for cauterizing tissue.

37. An apparatus as defined in claim 34, wherein said handle means further comprises a pistol grip, wherein said first control means comprises a suction push-button valve that is normally closed and permits the flow therethrough of said negative pressure when pressed to an open position and is located on said pistol grip, and wherein said second control means comprises an irrigation push-button valve that is normally closed and permits the flow therethrough of said irrigation stream when pressed to an open position and is located on said pistol grip, and wherein said third control means comprises an electric rocker switch having at least two positions for directing a high and low frequency voltage to said tip means and is located on said pistol grip, and wherein said fourth control means comprises a slidable blade-moving member extending through a slot in said pistol grip and is located on said pistol grip, and wherein said fifth control means comprises a blade-rotation member attached to a proximal end of said elongated tube so as to operatively turn said elongated tube and said tip means relative to said handle means and is located on said pistol grip.

38. A multi-functional endoscopic probe apparatus comprising:

an elongated tube comprising a multi-lumen having at least first, second, and third lumens therethrough and an electro-surgical tip comprising an elongated metallic member slidably situated in one of said lumens for the selective electro-surgical cutting and cauterizing at a distal end of said elongated tube;

first application means for applying a negative pressure to said second lumen of said elongated tube and connected to said second lumen such that the negative pressure is selectively applied to said second lumen;

second application means for applying an irrigation stream to said first lumen of said elongated tube and connected to said second lumen such that the fluid flow therethrough is selectively applied to a second one of said lumens;

third application means for applying an electric voltage to said tip means;

fourth application means for extending and retracting said tip means relative to the distal end of said elongated tube;

fifth application means for rotating said elongated tube and tip means relative to said handle means; and handle means for enabling said apparatus to be conveniently held and operatively controlled with one hand as to the plurality of functions provided by each of said application means, said handle means attached to a proximal end of said elongated tube, said handle means comprising:

first control means for selectively operating said first application means;

second control means for selectively operating said second application means and comprising first means for directing fluid flow to said second lumen, and second means for directing fluid flow to said third lumen;

third control means for selectively operating said third application means and comprising first means for the application of a voltage at a first frequency such that sufficient electrical energy is provided at said tip means for cutting tissue, and second means for the application of a voltage at a second frequency such that sufficient electrical energy is provided at said tip means for cauterizing tissue;

fourth control means for operating said fourth application means; and fifth control means for operating said fifth application means; and connector means for directing fluid flow, said connector means being responsive and selectively controlled at an outlet end thereof by one of said first control means and said first means for directing fluid flow, and said connector means being in fluid communication through an outlet end thereof with said second lumen.

39. An apparatus as defined in claim 38, wherein said handle means further comprises a pistol grip, wherein said first control means comprises a suction push-button valve that is normally closed and permits the flow therethrough of said negative pressure when pressed to an open position and is located on said pistol grip, and wherein said second control means comprises an irrigation push-button valve that is normally closed and permits the flow therethrough of said irrigation stream when pressed to an open position and is located on said pistol grip, and wherein said third control means comprises an electric rocker switch having at least two positions for directing a high and low frequency voltage to said tip means and is located on said pistol grip, and wherein said fourth control means comprises a slidable blade-moving member extending through a slot in said pistol grip and is located on said pistol grip, and wherein said fifth control means comprises a blade-rotation member attached to a proximal end of said elongated tube so as to operatively turn said elongated tube and said tip means relative to said handle means and is located on said pistol grip.

* * * * *

UNITED STATES PATENT AND TRADEMARK OFFICE
CERTIFICATE OF CORRECTION

PATENT NO. : 5,254,117
DATED : October 19, 1993
INVENTOR(S) : LARRY RIGBY et al.

It is certified that error appears in the above-indentified patent and that said Letters Patent is hereby corrected as shown below:

Title page, item [57], col. 2,
Abstract, lines 22-23, "cauterized" should be --cauterize--
Column 2, line 37, delete "as well"
Column 3, line 65, "An" should be --A--
Column 4, line 25, "and cutting tip," should be --the cutting tip--
Column 4, line 26, "floor" should be --flood--
Column 5, lines 35-36, "FIGS. 5 and 6" should be --FIG. 5--
Column 7, lines 29-30, "above-describe" should be --above-described--
Column 11, line 12, "fourth the" should be --the fourth--
Column 14, line 23, "claims 1" should be --claims 1 or 2--
Column 14, line 38, "second one of said lumens." should be --second lumen.--
Column 16, line 2, "piston" should be --pistol--
Column 16, line 4, "piston" should be --pistol--
Column 16, line 6, "piston" should be --pistol--
Column 16, line 8, "piston" should be --pistol--

Signed and Sealed this

Seventh Day of June, 1994

Attest:

BRUCE LEHMAN

*Attesting Officer*  *Commissioner of Patents and Trademarks*